(12) United States Patent
Capannoli et al.

(10) Patent No.: US 8,163,296 B2
(45) Date of Patent: Apr. 24, 2012

(54) DIMENSIONAL ANALYSIS OF SACCHARIDE CONJUGATES WITH GPC AND SEC-MALS

(75) Inventors: Giorgio Capannoli, Siena (IT); Valeria Carinci, Siena (IT); Sandro D'Ascenzi, Siena (IT); Claudia Magagnoli, Siena (IT)

(73) Assignee: Novartis AG, Basel (CH)

( * ) Notice: Subject to any disclaimer, the term of this patent is extended or adjusted under 35 U.S.C. 154(b) by 1038 days.

(21) Appl. No.: 11/630,545

(22) PCT Filed: Jun. 21, 2005

(86) PCT No.: PCT/IB2005/002532
§ 371 (c)(1),
(2), (4) Date: Feb. 1, 2008

(87) PCT Pub. No.: WO2006/000920
PCT Pub. Date: Jan. 5, 2006

(65) Prior Publication Data
US 2008/0248059 A1  Oct. 9, 2008

(30) Foreign Application Priority Data

Jun. 21, 2004 (GB) .................................. 0413868.1

(51) Int. Cl.
*A61K 39/095* (2006.01)
*A61K 39/00* (2006.01)
*A61K 38/00* (2006.01)

(52) U.S. Cl. ............... 424/250.1; 424/184.1; 424/249.1; 530/300

(58) Field of Classification Search .................. None
See application file for complete search history.

(56) References Cited

FOREIGN PATENT DOCUMENTS

| WO | WO 02/058737 | * | 8/2002 |
|---|---|---|---|
| WO | WO 02/058737 A2 | * | 9/2002 |
| WO | WO 2004/032958 | | 4/2004 |
| WO | WO 2004/067030 | | 8/2004 |
| WO | WO 2005/032583 | | 4/2005 |
| WO | WO 2005/103230 | | 11/2005 |

OTHER PUBLICATIONS

D'Ambra, A.J. et al, "Absolute Molecular-Size and Molar-Mass Analysis of Meningococcal and Pneumococcal Conjugates and Polysaccharide . . . " Dev Biol, 103; 241-242 (2000).
Jumel, K. et al, "Evaluation of meningococcal C oligosaccharide conjugate vaccines by size-exclusion chromatography . . . " Biotechnol. Appl. Biochem., 36 (3); 219-226 (2002).
Lemercinier, X et al, "Analytical Procedures Used in the Control of Bacterial Glycoconjugate Vaccines," Pharmaceutical Sciences, 3 (1); 19-23 (1997).
Peltola, H., "Meningococcal Vaccines: Current Status and Future Possibilities," Drugs, 55 (3); 347-366 (1998).
Ho, M. et al, "Assessment of the stability and immunogenicity of meningococcal oligosaccharide C-CRM197 conjugate vaccines," Vaccine, 19; 716-725 (2001).
Von Hunolstein, C. et al, "A routine high-performance size-exclusion chromatography to determine molecular size distribution of *Haemophilus* . . . " Vaccine, 17 (2); 118-125 (1999).

* cited by examiner

*Primary Examiner* — Vanessa L. Ford
(74) *Attorney, Agent, or Firm* — Helen Lee; Robert Gorman; Otis Littlefield (57) ABSTRACT

GPC (gel permeation chromatography) and size exclusion chromatography with detection by multi-angle light scattering photometry (SEC-MALS) can be used to accurately measure molecular size and molar mass, respectively, of saccharide conjugates. The invention provides (a) a process for measuring the molecular size of a conjugated saccharide antigen within a sample, comprising a step of analyzing the sample by GPC, and (b) a process for measuring the molar mass of a conjugated saccharide antigen within a sample, comprising a step of analysing the sample by SEC-MALS.

2 Claims, 5 Drawing Sheets

DIMENSIONAL ANALYSIS OF SACCHARIDE CONJUGATES WITH GPC AND SEC-MALS

All documents cited herein are incorporated by reference in their entirety.

RELATED APPLICATIONS

This application is the U.S. National Phase of International Application No. PCT/IB2005/002532, filed Jun. 21, 2005 and published in English, which claims priority to Great Britain Application No. 0413868.1, filed Jun. 21, 2004. The teachings of the above applications are incorporated herein in their entirety by reference.

TECHNICAL FIELD

This invention is in the field of analysis and quality control of vaccines that include bacterial capsular saccharides that are conjugated to a carrier.

BACKGROUND ART

Immunogens comprising capsular saccharide antigens conjugated to carrier proteins are well known in the art. Conjugation converts T-independent antigens into T-dependent antigens, thereby enhancing memory responses and allowing protective immunity to develop, and the prototype conjugate vaccine was for *Haemophilus influenzae* type b (Hib) [e.g. see chapter 14 of ref. 1]. Since the Hib vaccine, conjugated saccharide vaccines for protecting against *Neisseria meningitidis* (meningococcus) and against *Streptococcus pneumoniae* (pneumococcus) have been developed. Other organisms where conjugate vaccines are of interest are *Streptococcus agalactiae* (group B streptococcus) [2], *Pseudomonas aeruginosa* [3] and *Staphylococcus aureus* [4].

Rather than use full-length capsular saccharides, it is possible to select oligosaccharide fragments of desired size after a hydrolysis step [e.g. ref. 5], and it has been reported that conjugates made with intermediate chain-length oligosaccharides offer improved immunogenicity [e.g. refs. 6 & 7]. Of the three *N. meningitidis* serogroup C conjugated vaccines that have been approved for human use, MENJUGATE™ (*N. meningitidis* serogroup C oligosaccharide conjugate vaccine) [8] and MENINGITEC™ (*N. meningitidis* serogroup C oligosaccharide conjugate vaccine) are based on oligosaccharides, whereas NEISVAC-C™ (*N. meningitidis* serogroup C polysaccharide conjugate vaccine) uses full-length polysaccharide.

Where conjugates are included in a vaccine, quality control for manufacturing and release generally requires that they have a defined molecular size and/or molar mass, and also that these parameters are consistent between batches. Molecular size and molar mass can also be used for monitoring vaccine stability, as conjugates can aggregate over time, causing an increase in size and mass.

It is an object of the invention to provide new and improved methods for measuring molecular size, molar mass and related parameters for conjugated saccharide antigens, in particular for conjugates of meningococcal saccharides.

DISCLOSURE OF THE INVENTION

The inventors have discovered that gel permeation chromatography and SEC-MALS (size exclusion chromatography with detection by multi-angle light-scattering photometry) can be used to accurately and reliably measure molecular size and molar mass, respectively, of saccharide conjugates.

Thus the invention provides a process for measuring the molecular size of a conjugated saccharide antigen within a sample, comprising a step of analysing the sample by gel permeation chromatography. The retention time from the chromatography analysis can be converted into a viscosity radius (Rη) e.g. by comparison to a calibration curve, thereby permitting simple calculation of the molecular size. The average molecular size and/or distribution of molecular sizes of conjugates in the sample can easily be determined in this way.

The invention also provides a process for measuring the molar mass of a conjugated saccharide antigen within a sample, comprising a step of analysing the sample by SEC-MALS. The SEC retention time can be converted into molar mass. The average molar mass and/or distribution of molar mass (polydispersity) of conjugates in the sample can easily be determined in this way. Reference 9 reports that SEC-MALS has previously been used for measuring pre-conjugation pneumococcal and meningococcal saccharides, but no post-conjugation data are reported.

The Saccharide

The invention allows measurement of parameters for conjugated saccharide antigens. The saccharide antigen is typically a bacterial capsular saccharide e.g. from *Neisseria meningitidis* a (serogroups A, B, C, W135 or Y), *Streptococcus pneumoniae* (serotypes 4, 6B, 9V, 14, 18C, 19F, or 23F), *Streptococcus agalactiae* (types Ia, Ib, II, III, IV, V, VI, VII, or VIII), *Haemophilus influenzae* (typeable strains: a, b, c, d, e or f), *Pseudomonas aeruginosa*, *Staphylococcus aureus*, etc. Other saccharide analytes include glucans (e.g. fungal glucans, such as those in *Candida albicans*), and fungal capsular saccharides e.g. from the capsule of *Cryptococcus neoformans*. The invention is particularly useful for analysing capsular saccharides from serogroups A, C, W135 and Y of *N. meningitidis*.

The *N. meningitidis* serogroup A capsule is a homopolymer of ($\alpha$1→6)-linked N-acetyl-D-mannosamine-1-phosphate, with partial O-acetylation in the C3 and C4 positions. The *N. meningitidis* serogroup B capsule is a homopolymer of ($\alpha$2→8) linked sialic acids. The *N. meningitidis* serogroup C capsular saccharide is a homopolymer of ($\alpha$2→9) linked sialic acid (N-acetyl neuraminic acid, or 'NeuNAc'), with variable O-acetylation at positions 7 and/or 8. The *N. meningitidis* serogroup W135 saccharide is a polymer consisting of sialic acid-galactose disaccharide units [→4)-D-Neup5Ac(7/9OAc)-$\alpha$-(2→6)-D-Gal-$\alpha$-(1→], with variable O-acetylation at the 7 and 9 positions of the sialic acid [10]. The *N. meningitidis* serogroup Y saccharide is similar to the serogroup W135 saccharide, except that the disaccharide repeating unit includes glucose instead of galactose [→4)-D-Neup5Ac(7/9OAc)-$\alpha$-(2→6)-D-Glc-$\alpha$-(1→]. The *H. influenzae* type b capsular saccharide is a polymer of ribose, ribitol, and phosphate ['PRP', (poly-3-$\beta$-D-ribose-(1,1)-D-ribitol-5-phosphate)].

Other preferred saccharide antigens are eukaryotic saccharides e.g. fungal saccharides, plant saccharides, human saccharides (e.g. cancer antigens), etc. Other preferred saccharides are lipopolysaccharides and lipooligosaccharides.

The saccharide antigen can be in a form as found in nature, or can be in a derived form e.g. a saccharide that has been subjected to chemical alteration and/or depolymerisation. The invention is particular useful for analysing oligosaccharide fragments of capsular polysaccharides. Natural polysaccharides generally have a degree of polymerisation of at least 20 (e.g. 20, 30, 40, 50, 60 or more), and these may be converted into oligosaccharide fragments (e.g. with a degree of polymerisation of less than 20) by depolymerisation e.g. by hydrolysis.

Chemical hydrolysis of saccharides generally involves treatment with either acid or base under conditions that are standard in the art. Conditions for depolymerisation of capsular saccharides to their constituent monosaccharides are known in the art. For serogroup W135 and Y saccharides, acid hydrolysis is preferred. Acid hydrolysis using TFA (trifluoroacetic acid) can be used for hydrolysis of all of serogroups C, W135 and Y, with a slightly lower incubation temperature being preferred for serogroup C to avoid degradation of its sialic acids (90° C. rather than 100° C.). A typical TFA treatment involves addition of TFA to a final concentration of 2 M, followed by heating to 90-100° C. for 90 minutes. The serogroup C saccharide can be hydrolysed for total saccharide content analysis by treatment with 100 mM HCl at 80° C. for 2 hours [11]. Other typical hydrolysis conditions involve millimolar concentrations of a weak acid (e.g. acetic acid) at elevated temperatures (e.g. 70-80° C.).

The invention is particularly useful for use with conjugate samples that include various saccharides of different lengths e.g. different fragments of the same parent saccharide.

Conjugates

The saccharide antigen to be analysed is conjugated to a carrier. Covalent conjugation is used to enhance immunogenicity of saccharides by converting them from T-independent antigens to T-dependent antigens, thus allowing priming for immunological memory. Conjugation is particularly useful for pediatric vaccines and is a well known technique [e.g. reviewed in refs. 12 to 21]. Saccharides may be linked to carriers directly [22, 23], but a linker or spacer is generally used e.g. adipic acid, β-propionamido [24], nitrophenyl-ethylamine [25], haloacyl halides [26], glycosidic linkages [27], 6-aminocaproic acid [28], ADH [29], $C_4$ to $C_{12}$ moieties [30], etc.

Typical carrier proteins in conjugates are bacterial toxins or toxoids, such as diphtheria toxoid or tetanus toxoid. The CRM197 diphtheria toxin derivative [31-33] is the carrier protein in MENJUGATE™ and MENINGITEC™, whereas tetanus toxoid is used in NEISVAC™. Diphtheria toxoid is used as the carrier in MENACTRA™ (*N. meningitidis* serogroups ACWY oligosaccharide conjugates vaccine). CRM197 is the carrier protein in PREVNAR™ (Pneumococcal 13-valent Conjugate Vaccine). Other known carrier proteins include the *N. meningitidis* outer membrane protein [34], synthetic peptides [35,36], heat shock proteins [37,38], pertussis proteins [39,40], cytokines [41], lymphokines [41], hormones [41], growth factors [41], artificial proteins comprising multiple human $CD4^+$ T cell epitopes from various pathogen-derived antigens [42], protein D from *H. influenzae* [43,44], pneumococcal surface protein PspA [45], iron-uptake proteins [46], toxin A or B from *C. difficile* [47], etc. Compositions may use more than one carrier protein e.g. to reduce the risk of carrier suppression, and a single carrier protein might carry more than one saccharide antigen [48]. Conjugates generally have a saccharide:protein ratio (w/w) of between 1:5 (i.e. excess protein) and 5:1 (i.e. excess saccharide). Compositions may include free carrier protein in addition to the conjugates [49].

The invention is particularly suitable for analysing conjugates of meningococcal saccharides (serogroups A, C, W135 and Y) to CRM197 carrier. Such conjugates can be prepared by the methods disclosed in references 50-53. Preferred conjugates are those prepared according to reference 51 i.e. oligosaccharide fragments with a CRM197 carrier and an adipic acid linker.

Gel Permeation Chromatography

Gel permeation chromatography (GPC) is a well known and standard technique. The invention will generally use HPGPC (high performance GPC). The GPC techniques are used according to the invention to determine the hydrodynamic size (in a mixture, the average size and/or distribution of sizes) of a conjugate in a sample.

The retention time on a GPC column can be converted to a viscosity radius (Rη) by standard techniques. Typically, retention time on a column will be determined for standards of known molecular size, thereby permitting correlation of these two parameters. The molecular size of a conjugate can then be inferred from its retention time on the column. For example, calibration of a column using dextrans of known molecular size, and their retention times can be correlated with the viscosity radius using a third order polynomial equation [54,55]. The viscosity radius uses intrinsic viscosity and molecular mass to account for the effect that shape of the molecule has on retention.

In a heterogeneous mixture, the GPC technique can be used to determine both the average molecular size and/or distribution of molecular size in the mixture.

SEC-MALS

Size exclusion chromatography (SEC) is a well known technique. The results of separation can be analysed by multi-angle light-scattering (MALS) photometry and differential refractometry. This method can provide information on the distribution of molar mass and hydrodynamic radius (molecular size), confirmation and other physical parameters of a polymer, independent of chromatographic parameters such as flow rate and stationary phase and without the need for calibration for molar mass [9]. Rather than requiring calibration for molar mass, molecular mass determination by MALS is based on prior determination of the specific refractive index (dn/dc) for the polymer of interest in the solvent of interest at the wavelength and temperature of interest.

Thus SEC-MALS can be used to determine the molar mass of a conjugate. The molar mass of a sample is determined at each data slice of a SEC peak, as seen from a typical Debye plot, with molar mass being determined from the intercept of the plot [56-58]. Refractive index signal proportional to concentration, and the 90° MALS signal proportional to concentration and molar mass, can be superimposed to determine molar mass distributions.

In a heterogeneous mixture, the SEC-MALS technique can be used to determine both the average molar mass and/or distribution of molar mass polydispersity) in the mixture.

Conjugate Compositions

The invention provides a composition comprising a conjugate of a capsular saccharide from serogroup A *N. meningitidis*, wherein the molecular size of the conjugate is 57.1 Å and/or the molar mass of the conjugate is 88.5 kDa. The composition may also include a conjugate of a capsular saccharide from serogroup A *N. meningitidis*, wherein the molar mass of the conjugate is 190 kDa.

The invention provides a composition comprising a conjugate of a capsular saccharide from serogroup C *N. meningitidis*, wherein the molecular size of the conjugate is 57.0 Å and/or the molar mass of the conjugate is 85.2 kDa.

The invention provides a composition comprising a conjugate of a capsular saccharide from serogroup W135 *N. meningitidis*, wherein the molecular size of the conjugate is 68.7 Å and/or the molar mass of the conjugate is 110.1 kDa. The composition may also include a conjugate of a capsular saccharide from serogroup W135 *N. meningitidis*, wherein the molar mass of the conjugate is 347 kDa.

The invention provides a composition comprising a conjugate of a capsular saccharide from serogroup Y *N. meningitidis*, wherein the molecular size of the conjugate is 63.3 Å and/or the molar mass of the conjugate is 84.7 kDa. The composition may also include a conjugate of a capsular saccharide from serogroup Y *N. meningitidis*, wherein the molar mass of the conjugate is 486 kDa.

Although the above values for molecular size and molar mass are given as single figures, the invention extends to conjugates where these figures are ±20%, ±15%, ±10%, ±5%, ±2%, etc.

The invention also provides a composition comprising two or more (i.e. 2, 3, or 4) of the serogroup A, C, W135 and Y conjugates as described above.

The invention also provides a process for preparing a multivalent conjugate vaccine, comprising the steps of (a) analysing two or more conjugates using a method of the invention, and (b) combining the analysed conjugates to form the multivalent vaccine.

The invention also provides a process for preparing a multivalent conjugate vaccine, comprising the steps of mixing two or more conjugates that have been analysed using a method of the invention.

Mixed Saccharides

The invention allows analysis in compositions that comprise conjugates of capsular saccharides. In general, the invention will be used for samples containing a single type of conjugate (i.e. saccharides derived from the same capsular saccharide, linked to the same carrier). For multivalent conjugate vaccines (e.g. MENACTRA™, PREVNAR™), therefore, the invention will generally be used on individual conjugates before they are combined to make the final multivalent product, rather than on the final product itself. If two conjugates have very different molecular sizes and molar masses, however, then parallel analysis is straightforward.

Stability During Storage

The invention can be used to monitor stability of conjugates during storage. Thus the methods of the invention can be performed on samples from the same material at time t1 and t2 and the results of the analysis can be compared. A significant change in molar mass and/or molecular size indicates that the vaccine is not fully stable. Thus the invention can be used to select stable vaccines and reject unstable vaccines.

Non-Conjugate Components

As well as analysing conjugates in a composition, the processes of the invention may include analysis of other components or properties e.g. osmolality, pH, degree of polymerisation for individual saccharides or conjugates, protein content (particularly for carrier proteins), aluminium content, detergent content, preservative content, etc.

The invention provides a method for preparing a vaccine composition, comprising a step of molar mass and/or molecular size analysis of a conjugate according to the invention, and a step of pH measurement of the composition, optionally followed by a step of adjusting the pH of the composition to a desired value e.g. between 6 and 8, or about 7.

The invention also provides a method for preparing a vaccine composition, comprising the steps of: (a) providing one or more conjugates that have been as described above; (b) formulating the conjugate(s) into a bulk vaccine; (c) analysing the bulk vaccine for pH and/or other properties; and, if the results from step (c) indicate that the bulk vaccine is acceptable for clinical use, (d) preparing and packaging the vaccine for human use from the bulk. Step (c) may involve assessment of minimum saccharide concentration, assessment of unconjugated:conjugated saccharide ratio, etc. Step (d) may involve packaging into unit dose form or in multiple dose form e.g. into vials or into syringes. A typical human dose for injection has a volume of 0.5 ml.

The invention also provides a method for preparing a vaccine composition, comprising the steps of: (a) providing one or more conjugates that have been as described above; and (b) mixing the conjugated saccharide with one or more further antigens e.g. with

- a capsular saccharide antigen from serogroup C of *N. meningitidis*.
- a capsular saccharide antigen from serogroup A of *N. meningitidis*.
- a protein antigen from serogroup B of *N. meningitidis*.
- preparations of *N. meningitidis* serogroup B microvesicles [59], 'native OMVs' [60], blobs or outer membrane vesicles [e.g. refs. 61 to 66 etc.].
- a saccharide antigen from *Haemophilus influenzae* type b.
- an antigen from *Streptococcus pneumoniae*, such as polyvalent conjugated saccharide antigens [e.g. refs. 67 to 69].
- an antigen from hepatitis A virus, such as inactivated virus [e.g. 70, 71].
- an antigen from hepatitis B virus, such as the surface and/or core antigens [e.g. 71, 72].
- an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 73 & 74]. Cellular *pertussis* antigens may be used.
- a diphtheria antigen, such as a diphtheria toxoid [e.g. chapter 3 of ref. 75] e.g. the $CRM_{197}$ mutant [e.g. 76].
- a tetanus antigen, such as a tetanus toxoid [e.g. chapter 4 of ref. 75].
- polio antigen(s) [e.g. 77, 78], such as IPV.

Such antigens may be adsorbed to an aluminium salt adjuvant (e.g. a hydroxide or a phosphate). Any further saccharide antigens are preferably included as conjugates.

Conjugates of the invention may similarly be adsorbed to an aluminium salt adjuvant (e.g. a hydroxide or a phosphate), or they may be unadsorbed (e.g. free in solution).

Batch-to-Batch Consistency

The processes of the invention are reliable and consistent, and thus allow valid comparisons of different batches of conjugates. Different batches of conjugates can thus be prepared, assayed, and consistent batches can be selected for release and use in preparing conjugate vaccines, whereas aberrant batches can be rejected.

The invention provides two batches of a vaccine, wherein: (a) both of the batches of vaccine comprise: (i) a conjugate of a capsular saccharide from serogroup A of *Neisseria meningitidis*; (ii) a conjugate of a capsular saccharide from serogroup C of *Neisseria meningitidis*; (iii) a conjugate of a capsular saccharide from serogroup W135 of *Neisseria meningitidis*; (iv) a conjugate of a capsular saccharide from serogroup Y of *Neisseria meningitidis*; (b) the molecular size of the serogroup A saccharide in the first batch is $A_1$ and the molecular size of the serogroup A saccharide in the second batch is $A_2$; (c) the molecular size of the serogroup C saccharide in the first batch is $C_1$ and the molecular size of the serogroup C saccharide in the second batch is $C_2$; (d) the molecular size of the serogroup W135 saccharide in the first batch is $W_1$ and the molecular size of the serogroup W135 saccharide in the second batch is $W_2$; (e) the molecular size of the serogroup Y saccharide in the first batch is $Y_1$ and the molecular size of the serogroup Y saccharide in the second batch is $Y_2$; (f) the ratios $A_1/A_2$, $C_1/C_2$, $W_1/W_2$ and $Y_1/Y_2$ are each between 0.90 and 1.10, and preferably are each between 0.95 and 1.05.

The invention provides two batches of a Vaccine, wherein: (a) both of the batches of vaccine comprise: (i) a conjugate of a capsular saccharide from serogroup A of *Neisseria meningitidis*; (ii) a conjugate of a capsular saccharide from serogroup C of *Neisseria meningitidis*; (iii) a conjugate of a capsular saccharide from serogroup W135 of *Neisseria meningitidis*; (iv) a conjugate of a capsular saccharide from serogroup Y of *Neisseria meningitidis*; (b) the molar mass of the serogroup A saccharide in the first batch is $A_1$ and the molar mass of the serogroup A saccharide in the second batch is $A_2$; (c) the molar mass of the serogroup C saccharide in the first batch is $C_1$ and the molar mass of the serogroup C saccharide in the second batch is $C_2$; (d) the molar mass of the serogroup W135 saccharide in the first batch is $W_1$ and the molar mass of the serogroup W135 saccharide in the second batch is $W_2$; (e) the molar mass of the serogroup Y saccharide in the first batch is $Y_1$ and the molar mass of the serogroup Y saccharide in the second batch is $Y_2$; (f) the ratios $A_1/A_2$, $C_1/C_2$, $W_1/W_2$ and $Y_1/Y_2$ are each between 0.90 and 1.10, and preferably are each between 0.95 and 1.05.

The ratios specified in (f) may be based on a single sample from each batch being compared, but will typically be based on average values (e.g. means) from multiple samples of each batch. Thus the two batches may be subjected to multiple sampling, and each sample may be subjected to multiple measurements of $A_1$, $A_2$, $C_1$, $C_2$, $W_1$, $W_2$, $Y_1$, and $Y_2$, with averages then being calculated for each batch, and with the averages being used to calculate the necessary ratios.

Each batch (or lot) of vaccine will have been prepared separately. For example, two different batches can be made by separate mixings of the same bulk single conjugates, or by mixing bulk single conjugates that were separately prepared. Different samples of the same bulk mixture are not different batches, as these samples are not subject to the batch-to-batch variations that result from differences that arise when preparing mixtures of different conjugates.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

MODES FOR CARRYING OUT THE INVENTION

CRM197 conjugates of oligosaccharides from serogroups A, C, W135 and Y of meningococcus were prepared as generally described in reference 51. Each of these conjugates was analysed by HPGPC and SEC-MALS according to the invention.

HPGPC Analysis

Glycoconjugate vaccines generally consist of an array of glycoforms with a range of saccharides of different lengths, attached to a protein carrier at multiple sites. HPGPC was used to characterise the meningococcal glycoconjugates in terms of molecular size, by determining their hydrodynamic size and size distribution.

Figure 1:
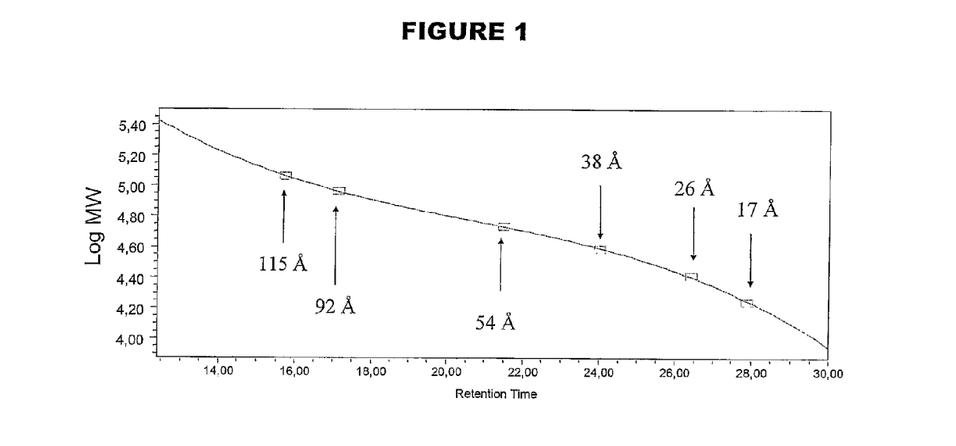
FIG. 1 shows a calibration curve of six dextrans of known hydrodynamic sizes.
Figure 2:
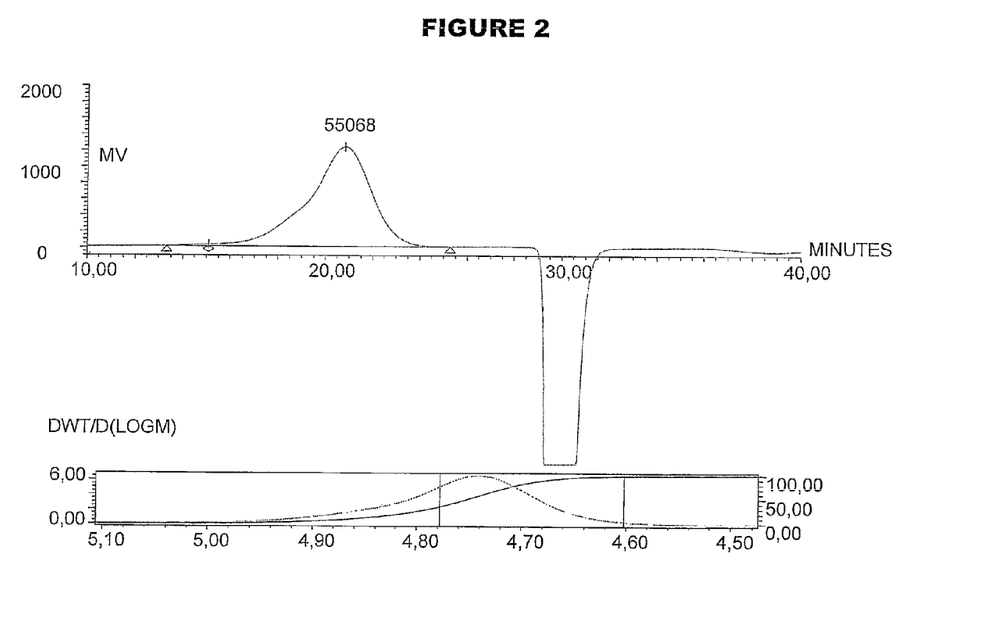
FIGS. 2 to 5 show HPGPC analysis of CRM197 conjugates from serogroups A, C, W135 and Y.
Figure 3:
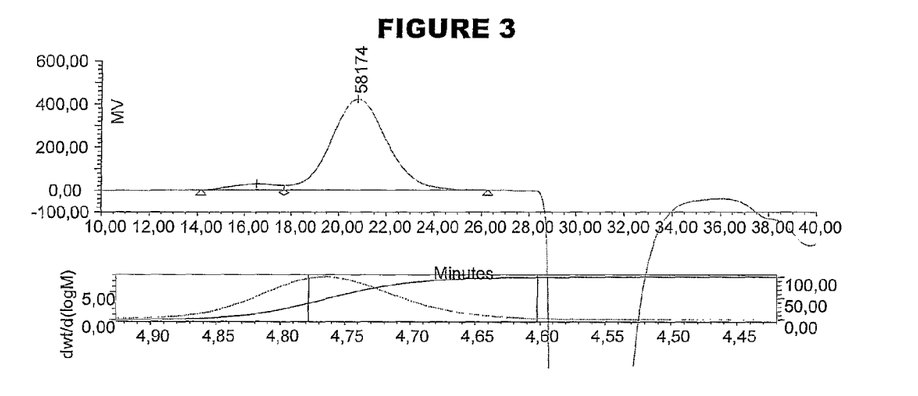
Figure 4:
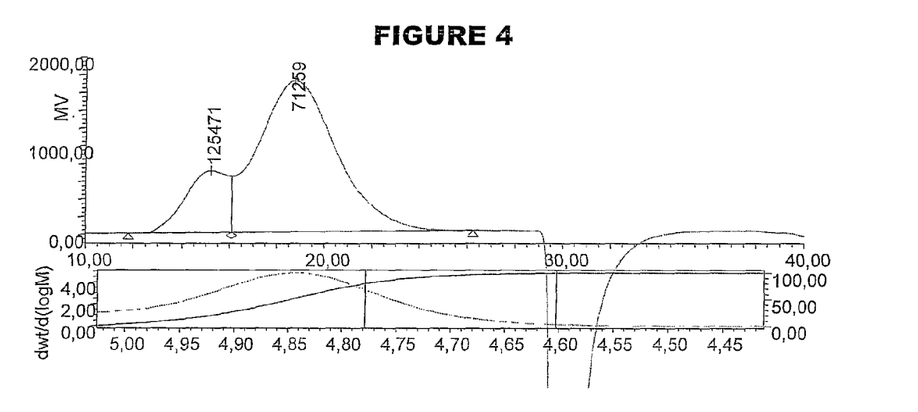
Figure 5:
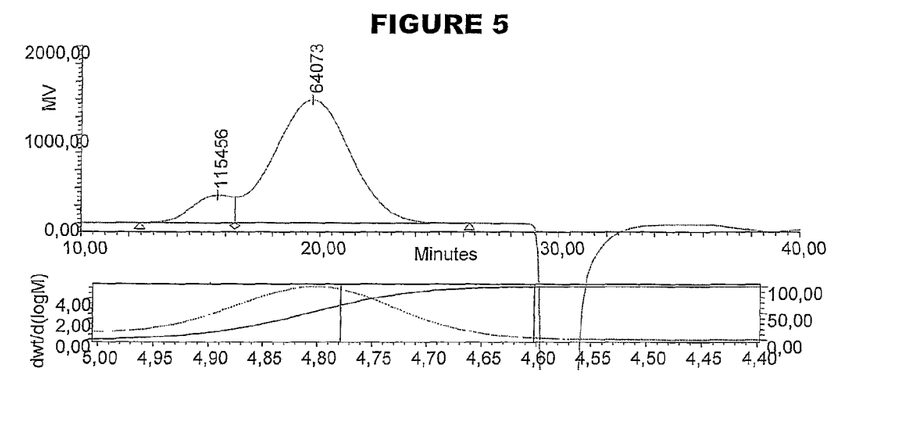

Calibration used a set of six dextrans with hydrodynamic size ranging from 17 to 115 Å. The HPGPC analysis of the standards in shown in FIG. 1. Standard molecular weights and calculated molecular weights were as follows:

| Standard   | 115360 | 54130 | 26000 | 91840 | 38560 | 17590 |
| Calculated | 115666 | 53847 | 25425 | 91514 | 39280 | 17767 |

The dextran analysis was used to correlate the viscosity radius (Rη) with the GPC retention time using a third-order polynomial equation [54,55]:

$$R\eta(\text{in Å}) = (10^8)(30 M_p[\eta]/(\pi \times 6.023 \times 10^{23}))^{1/3}$$

where: $M_p$=apical Mw and $[\eta]$=intrinsic viscosity in dL/g

The viscosity radii of the conjugates were calculated from this equation, which uses intrinsic viscosity and Mw to account for the effect that shape of the molecule has on retention.

The analyses of individual conjugates are shown in FIGS. 2 to 5. The hydrodynamic sizes were calculated as follows:

| Serogroup | A | C | W135 | Y |
|---|---|---|---|---|
| Size (Å) | 57.1 | 57.0 | 68.7 | 63.3 |
| Polydispersity | 1.032 | 1.018 | 1.040 | 1.035 |

As example conditions for the analysis, the serogroup A conjugate was analysed in a 50 μl injection volume on a TSK-Gel G4000SW (300×7.5 mm ID), with a 0.1M sodium phosphate/0.2M ammonium sulphate mobile phase, pH 7.0. The flow rate was 0.5 ml/min. A Waters 410 refaction index detector was used.

SEC-MALS Analysis

Figure 6:
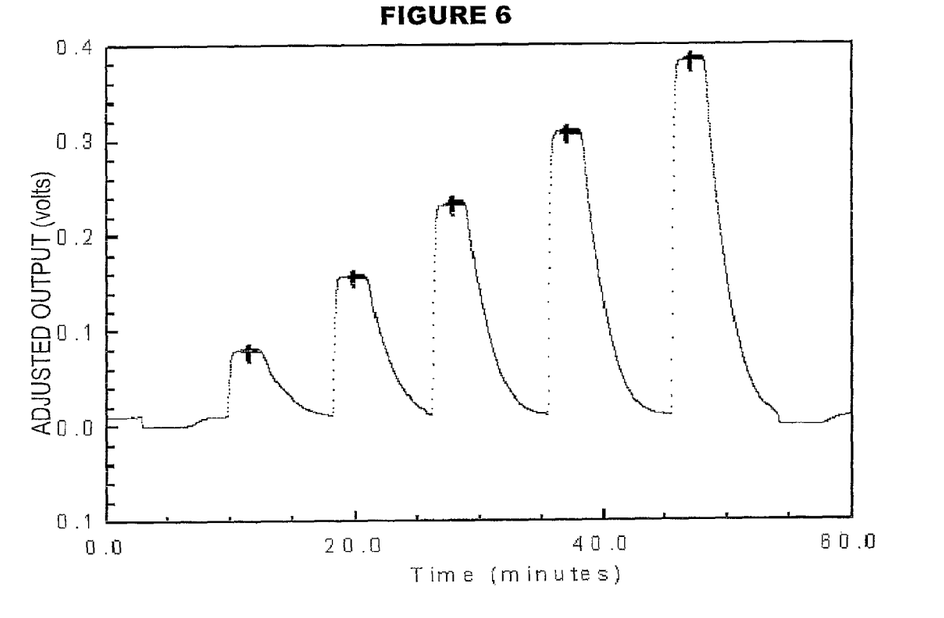
FIG. 6 shows the adjusted voltage output of known concentrations, for dn/dc calibration in FIGS. 7 and 8.
Figure 7:
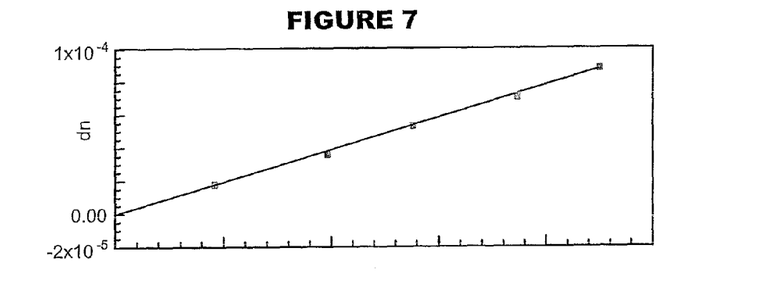
Figure 8:
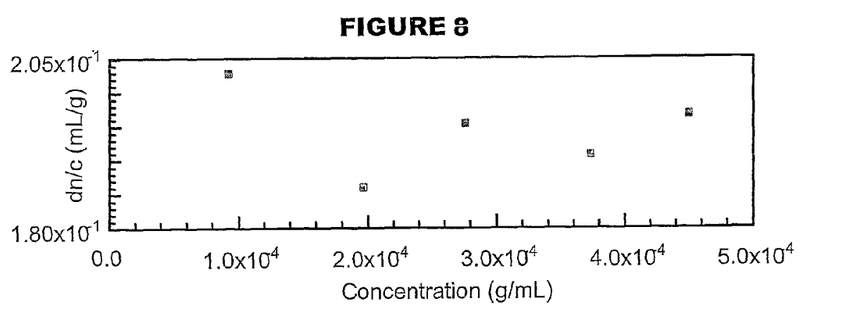

Prior to SEC-MALS analysis, the refractive indices (dn/dc) of the conjugates were determined under the analysis conditions. An example volt output for set concentration is shown in FIG. 6. This output leads to the standard curves shown in FIGS. 7 and 8. Calculated values were as follows:

| Serogroup | A | C | W135 | Y |
|---|---|---|---|---|
| dn/dc | 0.163 | 0.190 | 0.159 | 0.201 |

Figure 9:
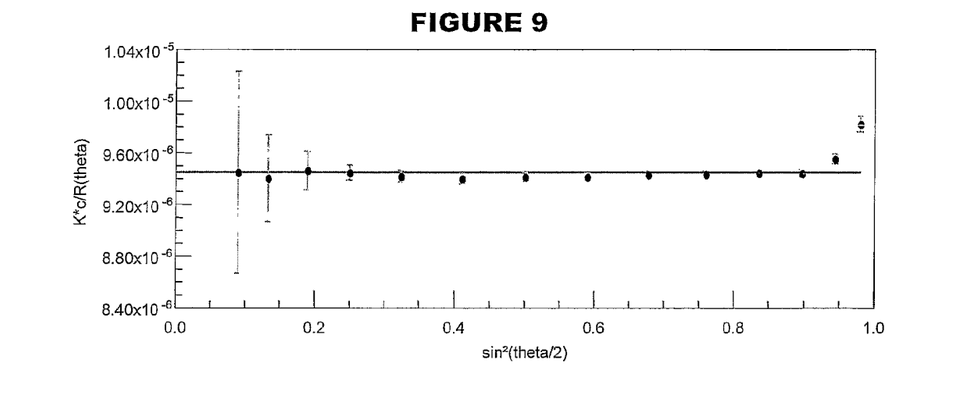
FIG. 9 shows a Debye plot from SEC-MALS.
Figure 10:
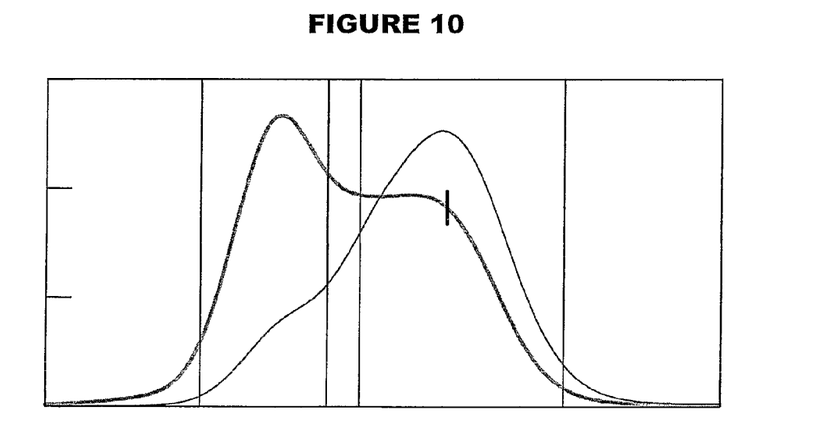
FIG. 10 shows a superimposition of RI signal and the 90° MALS signal.
Figure 11:
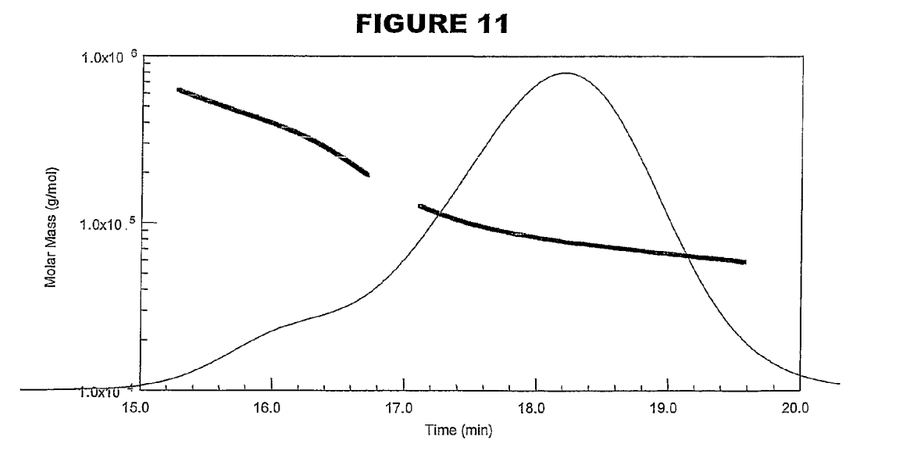
FIGS. 11 to 14 show molar mass analyses by SEC-MALS for CRM197 conjugates from serogroups A, C, W135 and Y.
Figure 12:
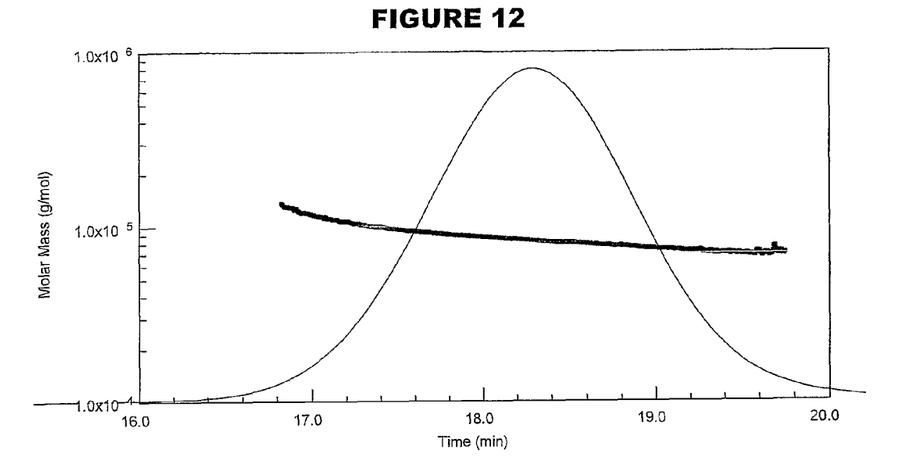
Figure 13:
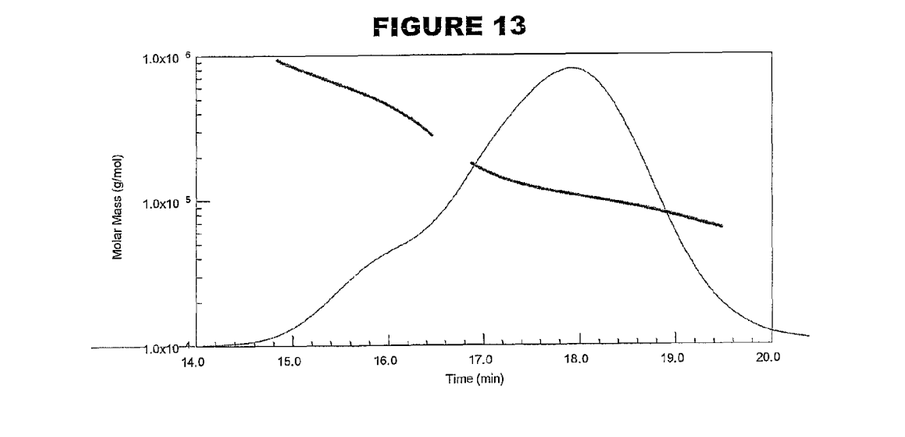
Figure 14:
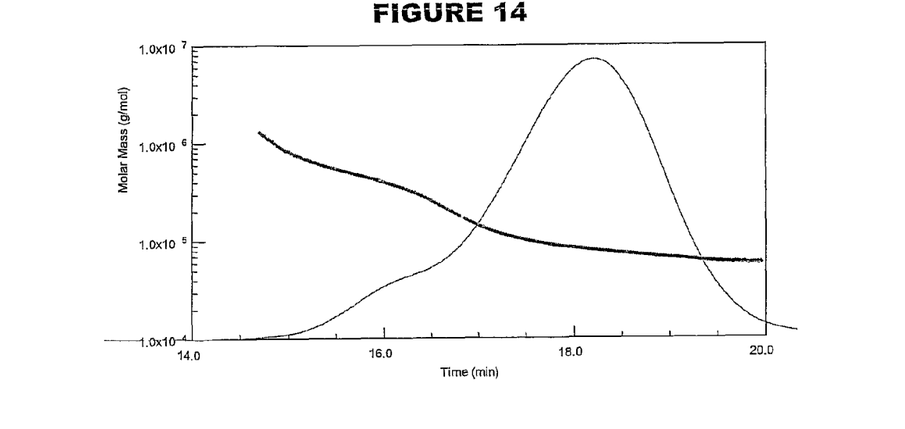

The conjugates were analysed by SEC-MALS. The molar mass of the samples were determined at each data slice of a SEC peak, as seen from a typical Debye plot in FIG. 9. The molar mass was determined from the intercept of the plot [56-58]. The RI signal (blue), proportional to concentration, and the 90° MALS detector (red), proportional to concentration and molar mass, can be superimposed (FIG. 10).

The analyses of molar mass (grams per mole) are shown in FIGS. 11 to 14. The analyses show that the MenA, MenW135 and MenY glycoconjugates have a major peak with a low concentration shoulder of higher MW, while the MenC conjugate has a single peak of more homogeneous material.

The results of the analyses for the peaks (MW in kDa; polydispersity in Mw/Mn) were as follows:

|  |  | A | C | W135 | Y |
|---|---|---|---|---|---|
| Major peak | MW | 88.540 | 85.230 | 110.100 | 84.650 |
|  | Polydispersity | 1.012 | 1.011 | 1.049 | 1.050 |
| Shoulder | MW | 190.000 | — | 485.800 | 347.200 |
|  | Polydispersity | 1.053 | — | 1.090 | 1.096 |

It will be understood that the invention has been described by way of example only and modifications may be made whilst remaining within the scope and spirit of the invention.

REFERENCES

The Contents of which are Hereby Incorporated by Reference

[1] *Vaccines* (eds. Plotkin et al.) 4th edition, ISBN: 0721696880.
[2] Baker et al. (2003) *J Infect Dis* 188:66-73.
[3] Theilacker et al. (2003) *Infect Immun* 71:3875-84.
[4] Anonymous (2003) *Drugs R D* 4:383-5.
[5] Ravenscroft et al. (1999) *Vaccine* 17:2802-2816.
[6] Paoletti et al. (1992) *J Clin Invest* 89:203-9.
[7] Anderson et al. (1986) *J Immunol* 137:1181-6.
[8] Jones (2001) *Curr Opin Investig Drugs* 2:47-49.
[9] D'Ambra et al. (2000) *Dev Biol Basel* 103:241-242.
[10] WO2005/033148.
[11] Jumel et al. (2002) *Biotechnol Appl Biochem* 36:219-226.
[12] Ramsay et al. (2001) *Lancet* 357(9251): 195-196.
[13] Lindberg (1999) *Vaccine* 17 Suppl 2:S28-36.
[14] Buttery & Moxon (2000) *J R Coll Physicians Lond* 34:163-168.
[15] Ahmad & Chapnick (1999) *Infect Dis Clin North Am* 13:113-133, vii.
[16] Goldblatt (1998) *J. Med. Microbiol.* 47:563-567.
[17] European patent 0477508.
[18] U.S. Pat. No. 5,306,492.
[19] WO98/42721.
[20] *Conjugate Vaccines* (eds. Cruse et al.) ISBN 3805549326, particularly vol. 10:48-114.
[21] Hermanson (1996) *Bioconjugate Techniques* ISBN: 0123423368 or 012342335X.
[22] U.S. Pat. No. 4,761,283
[23] U.S. Pat. No. 4,356,170
[24] WO00/10599
[25] Gever et al. Med. Microbiol. Immunol, 165:171-288 (1979).
[26] U.S. Pat. No. 4,057,685.
[27] U.S. Pat. Nos. 4,673,574; 4,761,283; 4,808,700.
[28] U.S. Pat. No. 4,459,286.
[29] U.S. Pat. No. 4,965,338
[30] U.S. Pat. No. 4,663,160.
[31] Anonymous (January 2002) *Research Disclosure*, 453077.
[32] Anderson (1983) *Infect Immun* 39(1):233-238.
[33] Anderson et al. (1985) *J Clin Invest* 76(1):52-59.
[34] EP-A-0372501.
[35] EP-A-0378881.
[36] EP-A-0427347.
[37] WO93/17712
[38] WO94/03208.
[39] WO98/58668.
[40] EP-A-0471177.
[41] WO91/01146
[42] Falugi et al. (2001) *Eur J Immuno* 31:3816-3824.
[43] EP-A-0594610.
[44] WO00/56360.
[45] WO02/091998.
[46] WO01/72337
[47] WO00/61761.
[48] WO99/42130
[49] WO96/40242
[50] WO02/058737.
[51] WO03/007985.
[52] Rennels et al. (2002) *Pediatr Infect Dis J* 21:978-979.
[53] Campbell et al. (2002) *J Infect Dis* 186:1848-1851.
[54] Kunitani et al. (1991) *J Chrom* 588:125ff.
[55] Kunitani et al. (1993) *J Chrom* 632:19ff
[56] Wyatt (1997) *Instrumentation Science & Technology* 25(1):1ff
[57] Wen et al. (1996) *Anal Biochem* 240:155ff.
[58] Rollings (1992) in *Laser Light Scattering in Biochemistry*, chapter 19.
[59] WO02/09643.
[60] Katial et al. (2002) *Infect Immun* 70:702-707.
[61] WO01/52885.
[62] European patent 0301992.
[63] Bjune et al. (1991) *Lancet* 338(8775):1093-1096.
[64] Fukasawa et al. (1999) *Vaccine* 17:2951-2958.
[65] WO02/09746.
[66] Rosenqvist et al. (1998) *Dev. Biol. Stand.* 92:323-333.
[67] Watson (2000) *Pediatr Infect Dis J* 19:331-332.
[68] Rubin (2000) *Pediatr Clin North Am* 47:269-285, v.
[69] Jedrzejas (2001) *Microbiol Mol Biol Rev* 65:187-207.
[70] Bell (2000) *Pediatr Infect Dis J* 19:1187-1188.
[71] Iwarson (1995) *APMIS* 103:321-326.
[72] Gerlich et al. (1990) *Vaccine* 8 Suppl:S63-68 & 79-80.
[73] Gustafsson et al. (1996) *N. Engl. J. Med.* 334:349-355.
[74] Rappuoli et al. (1991) *TIBTECH* 9:232-238.
[75] *Vaccines* (1988) eds. Plotkin & Mortimer. ISBN 0-7216-1946-0.
[76] Del Guidice et al. (1998) *Molecular Aspects of Medicine* 19:1-70.
[77] Sutter et al. (2000) *Pediatr Clin North Am* 47:287-308.
[78] Zimmerman & Spann (1999) *Am Fam Physician* 59:113-118, 125-126.

The invention claimed is:

1. A composition comprising a conjugate of a capsular saccharide from serogroup A *Neisseria meningitidis*, wherein the molecular size of the conjugate is 57.1±2% Å and/or the molar mass of the conjugate is 88.5±2% kDa.

2. A composition comprising two or more of the conjugates as defined in claim 1.

* * * * *